United States Patent

Rialdi

[11] Patent Number: 5,443,818
[45] Date of Patent: Aug. 22, 1995

[54] PROCESS FOR THE USE OF 4-ISOPROPYLBENZYL SALICILATE AS CUTANEOUS ANTILIPOPEROXIDANT

[76] Inventor: Giorgio Rialdi, 18, Via Semeria, Genova, Italy

[21] Appl. No.: 144,519

[22] Filed: Nov. 2, 1993

[30] Foreign Application Priority Data

Nov. 4, 1992 [IT] Italy .................. GE 92 A 000115

[51] Int. Cl.$^6$ .................. A61K 7/42; A61K 7/48; A61K 9/10
[52] U.S. Cl. ..................... 424/59; 514/938; 514/944
[58] Field of Search .................. 424/59, 60; 514/938, 514/944

[56] References Cited

PUBLICATIONS

Bruno et al., Chem. Abs., 1984, vol. 103 (18): 146954f.

*Primary Examiner*—Dale R. Ore
*Attorney, Agent, or Firm*—Larson & Taylor

[57] ABSTRACT

Use, as cutaneous anti-lipoperoxidant, of 4-isopropyl-benzyl salicylate, having the formula:

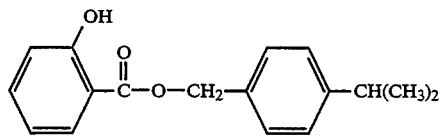

2 Claims, No Drawings

PROCESS FOR THE USE OF 4-ISOPROPYLBENZYL SALICILATE AS CUTANEOUS ANTILIPOPEROXIDANT

BACKGROUND OF THE INVENTION

The present invention relates to the compounds having antilipoperoxidizing action, especially the compounds performing such an action at a cutaneous level, usable in cosmetic-dermatologic formulations.

Relationships, between the pepoxidation of the polyunsaturated fatty acids of the biomembranes and cutaneous aging are known, for a long time at a cosmetologic research level; it is known that lipofuxine grains (aging pigment) that are essentially oxidated lipidic materials, are found in greater amount in humans and animals of advanced age.

Further, such peroxidative processes are in fact connected to carcinogenic processes; the origin of such processes is essentially connected to the presence of free radicals in the atmosphere and to the irradiation by the UV rays, and their inhibition has been widely studied in the last years.

Even the applicant have studied the use of a product containing isodecyl citrate, the ester of citric acid with isodecyl alcohol, which is able to perform antilipoperoxidizing activity, and which is sold under the proprietary name of Trioxene-LV by the Italian company Vevy Europe S. p.A..

SUMMARY OF THE INVENTION

In the context of a systematic research looking for verifying compounds having an antilipoperoxidizing UV filtering action it was denoted that a molecule formerly used by the same applicants as a sun-filter has shown certain features of an antilipoperoxidizing compound.

Such a compound is 4-isopropylbenzylsalicylate, of formula:

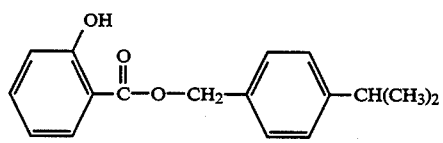

which is usually included in the bronzing formulations as a filtering factor.

The present invention relates to a new use of said 4-isopropylbenzylsalicylate as a compound having an antilipoperoxidizing action, especially for cutaneous treating.

A further feature of the present invention is the use of such a compound in cosmetic formulations of different kind, such as creams, liquid lotions or gels.

DESCRIPTION OF A PREFERRED EMBODIMENT OF THE INVENTION

The present invention will be more widely described by the way of a non limiting exemple.

In order to evaluate the effective ability of the 4-isopropylbenzylsalicylate (hereinafter referred as IPBS) to controlling the lipidic peroxidation, it was carried out an "in vitro" assay of lipidic peroxidation, particularly it dealt with the peroxidation induced by $FeSO_4$ under the classic schemes of such a process. (Esterbauer et al., Biochem. J., 208; 129-140, 1982).

At this end rat epatocites were used from male rats (variety: Sprague-Dawley, weight: 180-200 g). The epatocite suspensions, viable at 85%, were put in 25 ml plastic containers, in 4 ml of Hank solution, laking of $Ca^{2+}$ and $Mg^{2+}$; such a solution inhibits the aggregation between the cells.

The containers were then separated in four groups to which were applied the following treatments:
I group: control
II group: $FeSO_4$
III group: IPBS 500 μg/ml + $FeSO_4$ 200 μM
IV group: IPBS 1000 μg/ml + $FeSO_4$ 200 μM The containers were then incubated for 1 hour at 37° C. under stirring. At the end of incubation 1 ml samples are taken therefrom and subjected to the malondialdehyde under the technique of Ohkawa (Anal. Biochem. 95; 351-358, 1979) This technique includes the steps of lysis of the cellular material by the use of surfactants, and reaction over the lysate with thiobarbituric acid, wich reacts with malondialdehyde giving a dye. Such a dyeing product was then extracted with a butanole/pyridine mixture (15/1) and the dyeing in relieved with the spectrophotometer at 532 nm against blank.

The dosages of the proteins were performed with technique that uses the Coomassie Blue dye.

The results of booth dosages are reported in Table 1.

TABLE 1

| TREATMENT | MDA nM/ml | PROTEINS mg/ml | MDA/PROTEINS nM/mg |
|---|---|---|---|
| Control | N.D. | 1.22 | — |
| FeSO4 200M | 50.9 | 1.21 | 42.1 |
| IPBS 500 g/ml | 37.2 | 1.07 | 34.8 |
| IPBS 1000 g/ml | 28.9 | 1.06 | 27.3 |

N.D. = not dosable
MDA = malondialdheyde

From the data obtained in this way, it appears evidently that IPBS is of a remarkable antiperoxidizing ability. In fact, the concentration of Malondialdehyde in the samples decreases when increasing the IPBS concentration. This fact means certainly that the peroxidizing action of $FeSO_4$ is weaken by IPBS.

I claim:

1. A method of reducing lipidic peroxidation of the skin which comprises applying to the skin an effective amount of a composition consisting essentially of 4-isopropylbenzylsalicylate.

2. A method according to claim 1 wherein the composition is a lotion, cream or gel-containing 4-isopropylbenzylsalicylate as the active ingredient.

* * * * *